United States Patent [19]
Burkinshaw et al.

[11] Patent Number: 5,405,349
[45] Date of Patent: Apr. 11, 1995

[54] CUTTING JIG FOR POSTERIOR STABILIZED KNEE PROSTHESIS

[75] Inventors: Brian D. Burkinshaw; Wayne P. Gray, both of Pflugerville, Tex.

[73] Assignee: Intermedics Orthopedics, Inc., Austin, Tex.

[21] Appl. No.: 157,833

[22] Filed: Nov. 24, 1993

[51] Int. Cl.⁶ .............................................. A61B 17/56
[52] U.S. Cl. ........................................ 606/88; 606/82; 606/84
[58] Field of Search .................. 606/89, 79, 82, 84, 606/85, 87, 88, 167, 177

[56] References Cited

U.S. PATENT DOCUMENTS

| | | | |
|---|---|---|---|
| 4,349,058 | 9/1982 | Comparetto | 606/87 |
| 5,122,144 | 6/1992 | Bert et al. | 606/88 |

FOREIGN PATENT DOCUMENTS

| | | | |
|---|---|---|---|
| 104732 | 4/1984 | European Pat. Off. | 606/88 |
| 415837 | 3/1991 | European Pat. Off. | 606/87 |

Primary Examiner—Tamara L. Graysay
Attorney, Agent, or Firm—John R. Merkling

[57] ABSTRACT

An orthopedic jig or saw guide for preparing a femoral knee joint to receive the femoral component of a posterior stabilized prosthesis. The jig is adapted for cutting a central cavity in the distal end of the femur. In one embodiment, the cavity has a curved surface, the curve extending medial-laterally and a curved osteotome for incising a curved surface between the resulting two longitudinal incisions. The jig further comprises longitudinal saw guides for guiding a sagittal saw to make appropriate incisions parallel to the longitudinal axis of a femur.

15 Claims, 4 Drawing Sheets

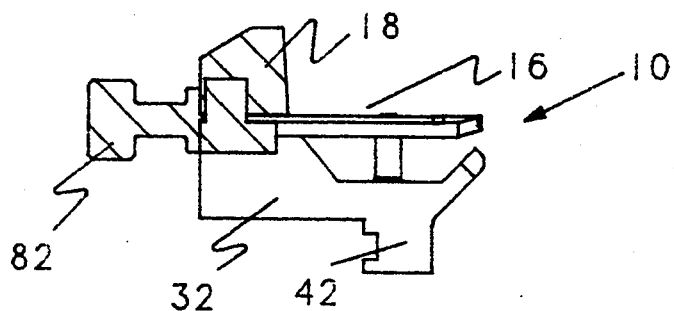
FIG. 3
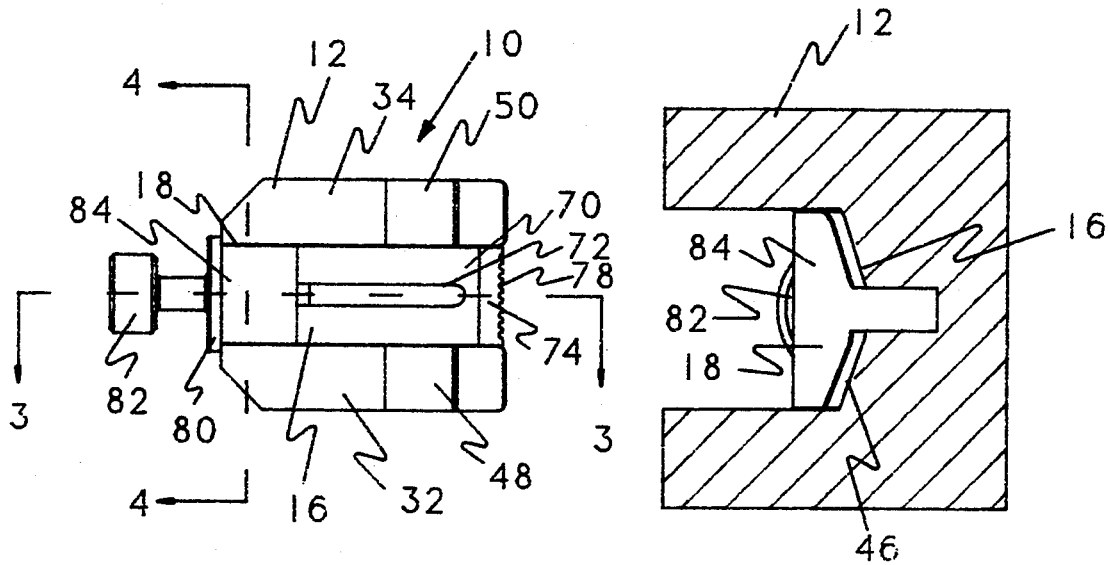
FIG. 2
FIG. 4

CUTTING JIG FOR POSTERIOR STABILIZED KNEE PROSTHESIS

BACKGROUND OF OUR INVENTION

Our invention relates to an orthopedic jig or saw guide for preparing a femoral knee joint to receive the femoral component of a posterior stabilized prosthesis.

The knee is the intermediate joint of the human leg. It is mainly a joint with one degree of freedom, that is, it bends in one plane. However, the knee has an accessory or second degree of freedom, rotation about the long axis of the leg, which occurs only when the knee is flexed. A replacement prosthesis, like the natural knee itself, must attempt to reconcile two mutually exclusive conditions. These are, first, to provide stability in extension, thus supporting the body weight, and, second, to provide mobility when the knee is flexed.

In the healthy knee, these requirements are met by a combination of bone structure and restraining ligaments. Many prosthetic knees attempt to retain these advantages by replacing only the bony structure or cartilage, while retaining the ligaments of the knee. In some cases, however, it is not possible to preserve all of the ligaments or the ligaments have themselves become substantially weakened. One of the known designs to accommodate such conditions is known generally as a posteriorly stabilized knee prosthesis. Such a structure is known, for example, from U.S. Pat. No. 4,213,209 to Install, et al. and U.S. Pat. No. 4,298,992 to Berstein, et al. The femoral component of a posterior stabilized knee prosthesis has, broadly speaking, two condyles separated by a central box or cavity. Posteriorly there is a transverse cam whose purpose will be explained below.

The tibial component of a posterior stabilized knee prosthesis is characterized by a central post, frequently part of a high density polyethylene articulating surface which is adapted to extend upwardly between the condyles of the femoral component and into the cavity mentioned above. This post, riding against medial and lateral walls of the cavity, gives addition stability to the prosthesis. Moreover, as the knee is bent, the transverse cam will contact the post on a specially designed cam follower surface causing the knee to flex in a more anatomical fashion.

The assignee of our invention has developed a posteriorly stabilized knee prosthesis similar of that described in the '992 patent. The central housing or cavity, however, has a curved roof on the cavity of the femoral component. We have developed a specialized jig for creating the necessary cavity in the distal end of a femur to receive such a posterior stabilized femoral component.

SUMMARY OF OUR INVENTION

Our invention comprises a jig for cutting a central cavity in the distal end of the femur, the cavity having a curved surface, the curve extending medial-laterally. Our invention comprises longitudinal saw guides for guiding a sagittal saw to make appropriate incisions parallel to the longitudinal axis of a femur and a curved osteotome for incising a curved surface between the resulting two longitudinal incisions.

With the foregoing in mind, it is an object of our invention to provide a jig which can assist a surgeon in replicably and accurately producing a curved cavity to receive a femoral component of a posterior stabilized knee prosthesis.

We will now describe our preferred embodiment with respect to the accompanying drawings.

BRIEF DESCRIPTION OF THE DRAWINGS

FIG. 2 is a distal view of the saw guide of our invention.

FIG. 3 is a through section of the jig taken along line 3—3 of FIG. 2.

FIG. 4 is a through section of the jig taken along line 4—4 of FIG. 2.

DETAILED DESCRIPTION OF OUR PREFERRED EMBODIMENT

We will now describe the preferred embodiment of our invention. Like numerals will be used to describe like parts in all the figures.

Figure 1:
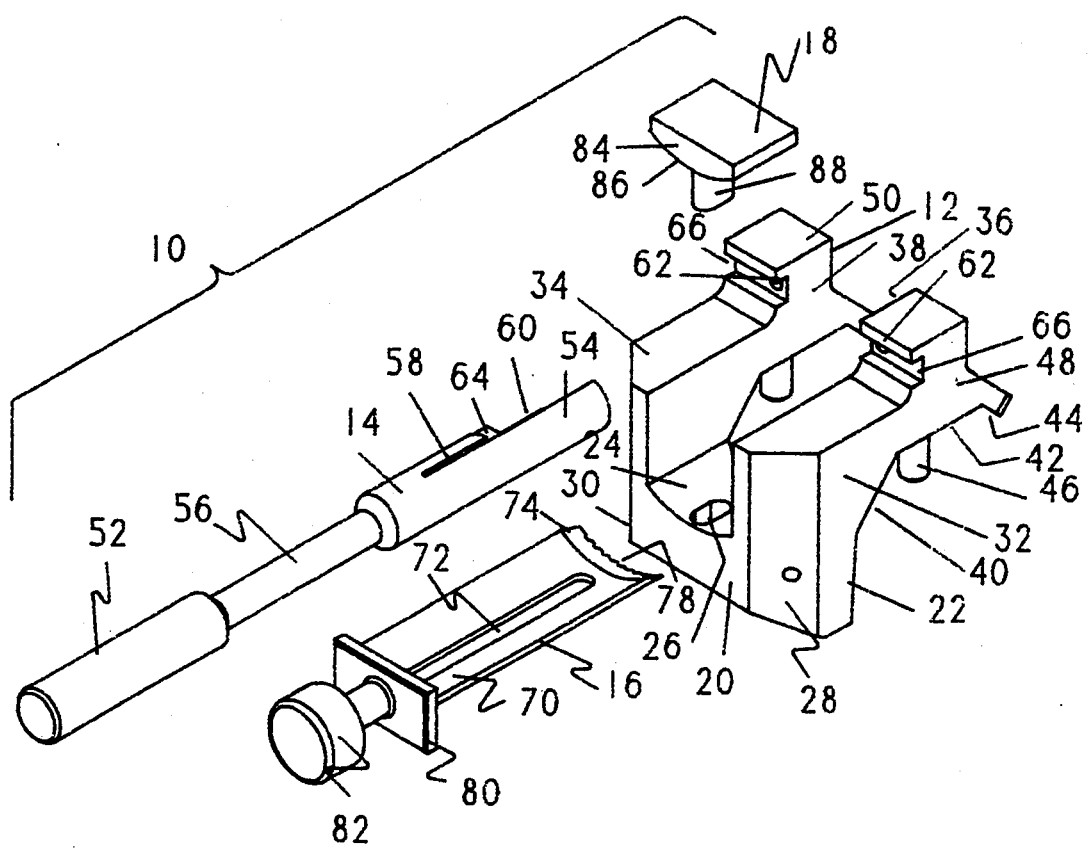
FIG. 1 is a perspective view of a jig according to our invention.

FIG. 1 shows a perspective view of a jig system, generally designated 10, according to our present invention. The jig system comprises a guide block 12, a sagittal saw capture guide 14, an osteotome or bone knife 16, and a capture block 18.

It will be understood that the guide block 12 is placed on a resected distal end of the femur. The initial resection of the femur is accomplished in a known manner and can take any of a number of forms which dictate some of the design of the guide block. Our preferred embodiment relates to a resected femur having four surfaces. Femoral components have knee prostheses which are adapted to such a geometry, but which do not of a posterior stabilized feature, have been available heretofore from Intermedics Orthopedics, Inc., the assignee of our invention. A femoral chamfer saw guide for creating the resected surfaces accurately has also been commercially available and need not be further described here.

The guide block 12 comprises an anterior body 20 having an anterior surface 22 adapted to lie adjacent a first resected plane on the femur. The body 20 has a curved surface 24 which receives the osteotome 16 in sliding contact. The surface 24 is curved medially-laterally but is generally linear in a posterior-anterior direction. Centrally on the curved surface 24 we have provided a slot 26 to receive the capture block 18, as will be more fully described below. At medial and lateral ends, 28, 30 respectively, of the body 20, arms 32, 34 extend distally from the body 20. The arms 32, 34 are preferably mirror images of each other. Each arm 32, 34 has a longitudinal surface 36, 38 which are generally parallel to the longitudinal axis of the femur when the guide block is in use. These surfaces 36, 38 are parallel to one another and spaced apart from one another. Each of the surfaces provides a part of a guide for sagittal saw to permit longitudinal cuts to be made. The proximal side of the arms comprise three walls 40, 42 and 44 which are adapted to abut resected surfaces on the femur when the jig is use. The central wall, wall 42, is generally parallel to the anterior-posterior extension of the curved surface 24. On the central surface 42, we have provided stabilizing pins 46 which fit into holes extending into the femur for accurate orientation of the jig.

Distal from the guide pins 46, on the opposite sides of the arms 32, 34 are housing 48, 50. These housings 48, 50 are used in conjunction with the sagittal saw capture guide 14. In our preferred embodiment, the sagittal saw capture guide 14 is a component previously available from our assignee. The sagittal saw capture guide 14 has a handle 52 and a head 54 connected by a shaft 56. The head 54 has a longitudinal slot 58 into which the blade of a sagittal saw can be inserted. An offset pin 60 extends on one side of the slot 58 and is adapted to be inserted into a bore 62 in the housing 48, 50. The sagittal saw capture guide 14 also has a generally rectangular block 64 adjacent the pin 60 for inhibiting rotation of the guide 14. This block 64 fits into a transverse slot 66 in the housing 48, 50 and prevents the guide 14 from pinching the sagittal saw by rotation. A sagittal saw is then inserted into the guide 14 and along one of the longitudinal walls 36, 38 to make longitudinal incisions in the femur. These incisions will be parallel to one another and generally aligned with a longitudinal axis of the patient's femur. When these cuts have been made, the sagittal saw may be set aside and the capture guide 14 removed. The osteotome 16 can then be laid on the curved surface 24 of the body 20 and secured thereto with the capture block 18. The osteotome is then driven with a hammer through the bone incising a curved surface between the longitudinal cuts. This removes a precise defined portion of bone for receiving the femoral component of the posterior stabilized knee prosthesis.

The osteotome 16 comprises a curved blade 70 having a central slot 72, a beveled edge 74 removes the bone in the manner of a chisel. Serrations 78 may also be provided to improve the cutting efficiency of the osteotome. A stop bock 80 on the opposite end of the blade prevents the osteotome from being driven out of the jig. An anvil 82 is also provided so that the osteotome may be driven into the bone using a hammer.

The capture block comprises a body 84 having a convex surface 86 which will ride against the blade 70 of the osteotome. A post 88 extends through the slot 72 of the osteotome and into the slot 26 in the body 20.

Figure 5:
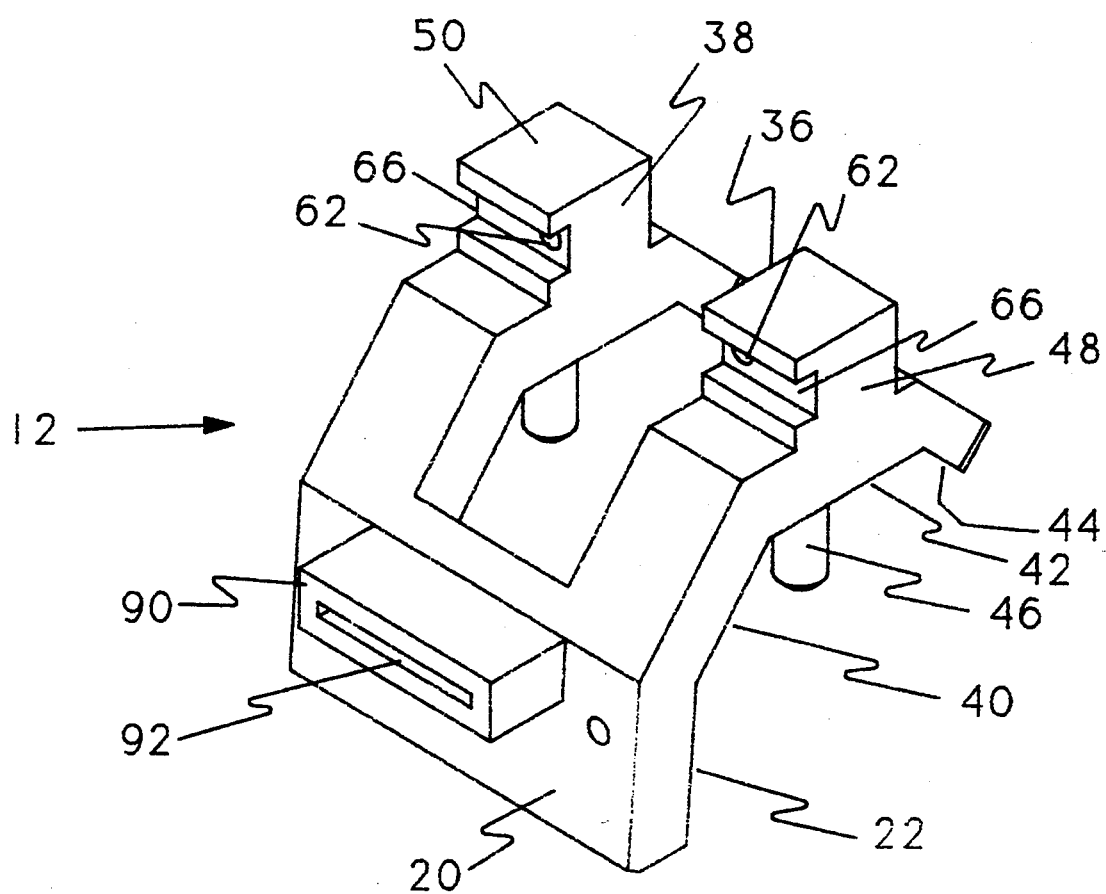
FIG. 5 is a perspective view of an alternative jig according to our invention.
Figure 6:
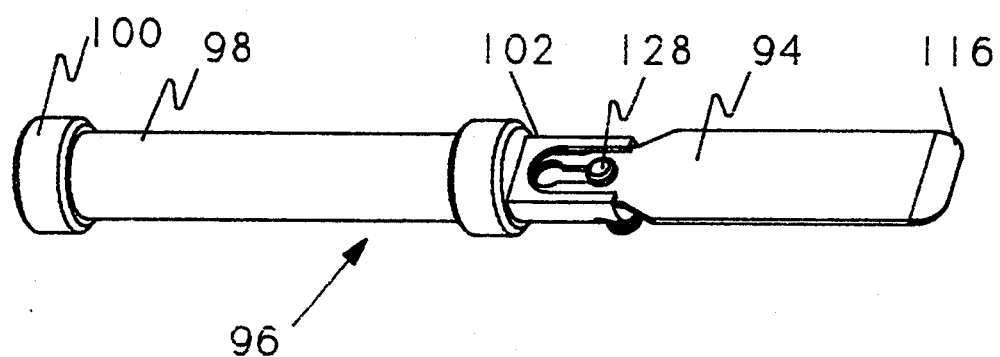
FIG. 6 is a perspective view of an osteotome for use with the jig of FIG. 5.
Figure 7:
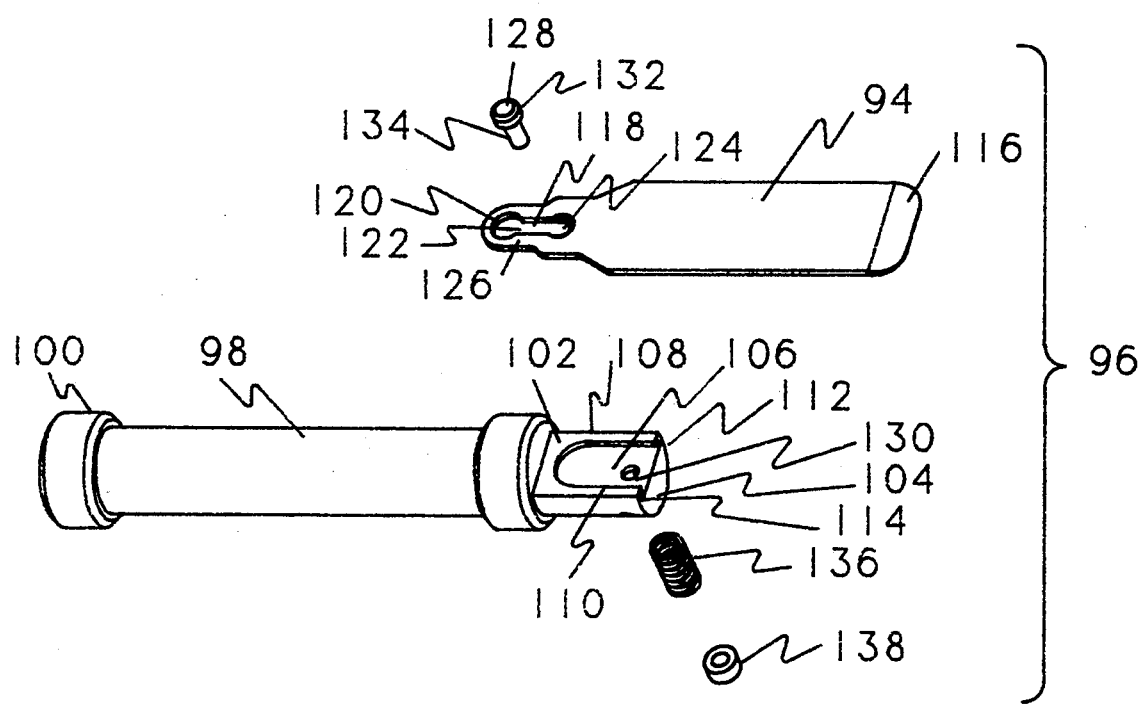
FIG. 7 is an exploded view of the osteotome of FIG. 6.

An alternative, and presently preferred, embodiment of a guide block 12a is illustrated in perspective view in FIG. 5. The embodiment of FIG. 5 differs from that of FIG. 1 in that it is specifically designed for a straight bladed osteotome. Those features common to the embodiments of FIGS. 1 and 5 are labeled with similar numerals and the explanation of those features will not be repeated here. The guide block of FIG. 5 has an extended block 90 with a straight slot 92 therein. This slot receives a flat blade 94 of an osteotome 96, illustrated in perspective view in FIG. 6. The osteotome 96 comprises a handle 98 to which the blade 94 is removeably attached. The handle has an anvil 100 which can be struck with a hammer or mallet to drive the blade through the bone. On the distal end of the handle 98 is a connector 102 for receiving the blade 94. The features of this connector can best be understood by reference to FIG. 7. The connector has a generally cylindrical body 104 with a flattened surface 106 thereon. The flattened surface 106 has two spaced apart parallel rails 108, 110 which define slots 112, 114 into which blade 94 may be inserted. The blade 94 has a cutting edge 116 distally and a reduced section 118 proximally which slides into the slots 112, 114. Also at the proximal end of the blade 94 is a keyhole slot 120. The keyhole 120 has a large through bore 122 proximally and a small through bore 124 distally connected by a straight slot 126. Adjacent the large through bore 122, the proximal end of the blade 94 is further reduced in width so that the blade can be laid between the rails 108, 110. A headed pin 128 is slidingly received in a through bore 130 in the connector. A head 132 of this pin generally rests against the flat surface of the connector. A shank 134 passes through the through bore 130 and is surrounded by a spring 136. A cap 138 is then placed on the shaft 134 to hold the spring 136 in place. By pressing against the cap 138, the head 132 of the pin 128 can be raised through the large through bore 122. The blade 94 can then slide into the slots 112, 114 until the head 132 sets into the smaller throughbore 124, thus locking the blade 94 to the handle 98. The blade 94 can then be driven effectively through the slot 92 in the jig of FIG. 5.

Our invention may be embodied in other specific forms by those of skill in the art without departing from the spirit or essential teachings thereof. The foregoing description is intended, therefore, to be illustrative and the scope of our invention is defined by the appended claims.

We claim as our invention:

1. An orthopedic apparatus for preparing a distal femoral surface of a patient to receive a femoral component of a knee prosthesis, said apparatus comprising in combination:

a guide block adapted to be temporarily positioned on a resected distal surface of a femur, said guide block having at least two spaced surfaces which are generally parallel to the longitudinal axis of the femur when the guide block is positioned thereon, and having an osteotome guide surface connecting said two spaced surfaces; and osteotome means for incising the distal end of the femur, said osteotome means having a convex surface adapted to be received in sliding contact on said guide surface, and having means for driving said osteotome means into said femur.

2. The orthopedic apparatus according to claim 1 wherein said at least two spaced surfaces are generally parallel to each other and generally perpendicular to said guide surface.

3. The orthopedic apparatus according to claim 2 further comprising a sagittal saw capture guide releasably connected to said guide block adjacent said spaced surfaces.

4. The orthopedic apparatus according to claim 1 wherein said guide surface is a concave surface and wherein said osteotome means comprises a curved cutting blade adapted to be received in sliding contact on said guide surface, said cutting blade forming said convex surface.

5. The orthopedic apparatus according to claim 4 wherein said at least two spaced surfaces are generally parallel to each other and generally perpendicular to said concave surface.

6. The orthopedic apparatus according to claim 5 further comprising a sagittal saw capture guide releasably connected to said guide block adjacent said spaced surfaces.

7. The orthopedic apparatus according to claim 6 further comprising means for restricting the motion of said osteotome means to linear motion along said concave surface.

8. The orthopedic apparatus according to claim 7 wherein said osteotome means further comprises a longitudinal slot and wherein said means for restricting comprises a block having a post for insertion through said slot and for connection to said guide block.

9. The orthopedic apparatus according to claim 4 wherein said cutting blade is serrated.

10. The orthopedic apparatus according to claim 9 wherein said at least two spaced surfaces are generally parallel to each other and generally perpendicular to said guide surface.

11. The orthopedic apparatus according to claim 10 further comprising a sagittal saw capture guide releasably connected to said guide block adjacent said spaced surfaces.

12. The orthopedic apparatus according to claim 11 further comprising means for restricting the motion of said osteotome means to linear motion along said guide surface.

13. The orthopedic apparatus according to claim 4 further comprising a sagittal saw capture guide releasably connected to said guide block adjacent said spaced surfaces.

14. The orthopedic apparatus according to claim 13 further comprising means for restricting the motion of said osteotome means to linear motion along said guide surface.

15. The orthopedic apparatus according to claim 14 wherein said osteotome means further comprises a longitudinal slot and wherein said means for restricting comprises a block having a post for insertion through said slot and for connection to said guide block.

* * * * *